(12) United States Patent
Guo et al.

(10) Patent No.: US 10,779,948 B2
(45) Date of Patent: Sep. 22, 2020

(54) ACETABULAR DEFECT RECONSTRUCTIVE PROSTHESIS

(71) Applicant: Beijing AK Medical Co., Ltd., Beijing (CN)

(72) Inventors: Wei Guo, Beijing (CN); Caimei Wang, Beijing (CN); Tao Ji, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 16/315,660

(22) PCT Filed: Jul. 8, 2016

(86) PCT No.: PCT/CN2016/089489
§ 371 (c)(1),
(2) Date: Jan. 7, 2019

(87) PCT Pub. No.: WO2018/006431
PCT Pub. Date: Jan. 11, 2018

(65) Prior Publication Data
US 2019/0224014 A1  Jul. 25, 2019

(51) Int. Cl.
*A61F 2/34* (2006.01)
*A61F 2/30* (2006.01)

(52) U.S. Cl.
CPC ............ *A61F 2/34* (2013.01); *A61F 2/30734* (2013.01); *A61F 2/30749* (2013.01); *A61F 2/30771* (2013.01); *A61F 2002/30062* (2013.01); *A61F 2002/3092* (2013.01); *A61F 2002/30332* (2013.01); *A61F 2002/30354* (2013.01); *A61F 2002/30405* (2013.01);
(Continued)

(58) Field of Classification Search
CPC .... A61F 2/34; A61F 2/30749; A61F 2/30771; A61F 2002/30405; A61F 2002/30428; A61F 2002/3092; A61F 2002/30354
USPC ...................................... 623/22.36
See application file for complete search history.

(56) References Cited

U.S. PATENT DOCUMENTS 5,176,711 A    1/1993  Grimes
5,916,268 A *  6/1999  Schollner ........... A61B 17/1746
                                                   623/22.36
(Continued)

FOREIGN PATENT DOCUMENTS

CN     1301241 A    6/2001
CN   103096841 A    5/2013
(Continued)

OTHER PUBLICATIONS

Extended European Search Report for EP patent application No. 16907935.7, dated Jul. 26, 2019.

*Primary Examiner* — Suba Ganesan
*Assistant Examiner* — Aren Patel
(74) *Attorney, Agent, or Firm* — Gang Yu

(57) ABSTRACT

The present disclosure provides an acetabular defect reconstructive prosthesis, comprising: an iliac support, the iliac support including a support seat (11) and a connecting wing plate (12) provided on the support seat (11), and the support seat (11) being contacted and matched with an ilium (1); and an acetabular cup (20) rotatably connected with the support seat (11) together. The technical solutions of the present disclosure can effectively solve the problems of reconstruction and long-term stability of a peri-acetabular defect in the related technology.

8 Claims, 8 Drawing Sheets

(52) U.S. Cl.
CPC .............. *A61F 2002/30428* (2013.01); *A61F 2002/30736* (2013.01); *A61F 2002/30838* (2013.01)

(56) References Cited

U.S. PATENT DOCUMENTS

| | | | |
|---|---|---|---|
| 6,572,655 B1* | 6/2003 | Johnson | A61F 2/30721 606/309 |
| 2004/0220673 A1* | 11/2004 | Pria | A61F 2/40 623/19.12 |
| 2005/0021148 A1* | 1/2005 | Gibbs | A61F 2/30724 623/22.12 |
| 2007/0142921 A1 | 6/2007 | Lewis et al. | |
| 2009/0177287 A1* | 7/2009 | Sala | A61F 2/30771 623/23.12 |
| 2013/0035766 A1 | 2/2013 | Meridew | |
| 2013/0066437 A1* | 3/2013 | Weeden | A61F 2/3609 623/22.36 |
| 2014/0265062 A1* | 9/2014 | Sanchez | A61F 2/34 264/642 |

FOREIGN PATENT DOCUMENTS

| | | | |
|---|---|---|---|
| CN | 103751853 A | 4/2014 | |
| CN | 106037996 A | 10/2016 | |
| DE | 4133433 C1 | 5/1993 | |
| EP | 1062922 A2 | 12/2000 | |
| WO | 2016086119 A1 | 6/2016 | |

\* cited by examiner

ACETABULAR DEFECT RECONSTRUCTIVE PROSTHESIS

TECHNICAL FIELD

The present disclosure relates to the field of medical devices, and more particularly, to an acetabular defect reconstructive prosthesis.

BACKGROUND

Peri-acetabular tumors include various primary malignant tumors, metastatic carcinomas, and benign tumors with relatively strong invasiveness such as bone giant cell tumor. Surgical excision is a primary method to treat pelvic tumors. As progresses have been made in surgical technologies, we now have the capability of performing widespread or eradicative surgical excision on the former and performing extensive and critical excision and scrapping on the later two. With the wide excision of the pelvic tumors, a relatively large bone defect will be caused generally, the continuity of a pelvis is interrupted, and partial soft tissues at the periphery are lost, so it is necessary to reconstruct the defective pelvis. The reconstruction methods differ depending on experience of an operator and different conditions of patients. Up to now, there haven't enough evidences to indicate which method is the best. The common reconstruction methods involve in a putting-aside therapy, a bone fusion, a structural allografting, a prosthesis reconstruction and the like, and three of which are described hereunder.

Putting-aside therapy: in 1978, Steel, et. al. firstly reported five cases suffering from acetabular peripheral chondrosarcoma received a hemipelvectomy in part or in whole. In an operation, a femoral head is put aside, is formed into a pseudarthrosis with an ilium stump, and is stabilized using a tension of peripheral soft tissues to form a flail hip. After the operation, the patients have a satisfactory motion in the hip with respect to adduction, abduction, flexion, extending and even to squat. However, it still has poor stability in the hip joint, as well as lower limb shortening and obvious deformity.

Simple bone fusion: this therapy is simple and easy to operate, and has good stability. But it loses the motion of joints and has a relatively high incidence rate of nonunion, fatigue fracture and infection. As a result of the simple fusion, serious lower limb shortening further may be caused, and particularly, a sacrum and an ilium are fused. The problem of the lower limb shortening can be solved by means of bone grafting and fusion, but yet, the complexity of the operation and the incidence rate of the nonunion are increased.

Prosthesis reconstruction saddle-like prosthesis reconstruction: a saddle-like prosthesis is originally designed by Nieder, et. al. due to a fact that the huge bone defect caused by revision after a total hip arthroplasty cannot be repaired. In 1983, Meulemeester used it first in the pelvic tumors and it has the advantages of relatively simple operation, flexible adjustment for a length of the prosthesis during the operation to correct lower limb discrepancy, no pain and no load in an early stage, etc. Thereafter, Nieder, Aboulafia, et. al. successively reported applications of the saddle-like prosthesis in acetabular tumor excision and reconstruction and considered that the effect is good. Currently, it is said that some cases with saddle-like prostheses replacement have achieved a certain effect. However, there are many postoperative complications, mainly in dislocation and deep infection.

SUMMARY

Some embodiments of the present disclosure provide an acetabular defect reconstructive prosthesis, so as to solve the problem that a hip joint is unstable after an operation in the related technology.

To this end, an embodiment of the present disclosure provides an acetabular defect reconstructive prosthesis, including: an iliac support, the iliac support including a support seat and a connecting wing plate provided on the support seat, and the support seat being contacted and matched with an ilium; and an acetabular cup rotatably connected with the support seat together.

In an exemplary embodiment, a side, contacted and matched with the ilium, of the connecting wing plate is provided with a micropore structure.

In an exemplary embodiment, a first screw hole is formed in the connecting wing plate; a first screw seat is arranged in the first screw hole; and the first screw seat is provided with a spherical inner surface.

In an exemplary embodiment, the side, contacted and matched with the ilium, of the connecting wing plate and/or a side, contacted and matched with the ilium, of the support seat are/is provided with a bio-coating.

In an exemplary embodiment, a first connection portion is provided on the support seat; and the acetabular cup includes a cup body, and a second connection portion provided on the cup body and matched with the first connection portion.

In an exemplary embodiment, the first connection portion is a first connecting cylinder; the second connection portion is a second connecting cylinder; and the first connecting cylinder and the second connecting cylinder are mutually nested together.

In an exemplary embodiment, a conical hole is provided inside the first connecting cylinder; the connecting cylinder is a conical cylinder; and the second connecting cylinder is inserted into the first connecting cylinder.

In an exemplary embodiment, the acetabular defect reconstructive prosthesis further includes a fastening screw; and the fastening screw sequentially passes through the acetabular cup, the support seat and the ilium so that the acetabular defect reconstructive prosthesis is fixed on the ilium.

In an exemplary embodiment, a second screw hole is formed in the support seat; a second screw seat is arranged in the second screw hole; and the second screw seat is provided with a spherical inner surface.

In an exemplary embodiment, the connecting wing plate is of a curved surface shape.

By applying the technical solutions of the present disclosure, the acetabular defect reconstructive prosthesis includes the iliac support, the iliac support includes the support seat and the connecting wing plate provided on the support seat, and the support seat is contacted and matched with the ilium. The above support seat and the connecting wing plate jointly support the ilium, so that a whole hip joint is more stable, and the problem that the hip joint is unstable after an operation in the related technology is solved. And in addition, the acetabular cup is rotatably connected with the support seat together, so owing to the above structure, a doctor may adjust a position of the acetabular cup according to a practical condition of a patient, the acetabular cup is guaranteed to be in a good installation angle and the problems of lower limb shortening and obvious deformity are improved.

BRIEF DESCRIPTION OF THE DRAWINGS

The accompanying drawings are described here to provide further understanding of the present disclosure, and form a part of the present disclosure. The schematic embodiments and description of the present disclosure are adopted to explain the present disclosure, and do not form improper limits to the present disclosure. In the drawings.

The above accompanying drawings include the following labels:

1. an ilium; 2. a sacrum; 11. a support seat; 111. a second screw hole; 12. a connecting wing plate; 121. a first screw hole; 13. a first connecting cylinder; 20. an acetabular cup; 21. a cup body; 211. an annular groove; 212. a through hole; 22. a second connecting cylinder; 30. a fastening screw; 40. a lining; 41. an installation space; 42. a lining groove; 50. a femoral stem; 51. a spherical head.

DETAILED DESCRIPTION OF THE EMBODIMENTS

It is to be noted that the embodiments of the present application and the characteristics of the embodiments may be combined with each other if there is no conflict. The present disclosure is described below with reference to the drawings and embodiments in detail.

As shown in FIG. 1 to FIG. 5, an acetabular defect reconstructive prosthesis of the embodiments includes an iliac support and an acetabular cup 20, wherein the iliac support includes a support seat 11 and a connecting wing plate 12 provided on the support seat 11; the support seat 11 is contacted and matched with an ilium 1; and the acetabular cup 20 is rotatably connected with the support seat 11 together.

By applying the technical solutions of the present disclosure, the acetabular defect reconstructive prosthesis includes the iliac support, the iliac support includes the support seat 11 and the connecting wing plate 12 provided on the support seat 11, and the support seat 11 is contacted and matched with the ilium 1. The above support seat 11 and the connecting wing plate 12 jointly support the ilium 1, so that a whole hip joint is more stable, and the problem that the hip joint is unstable after an operation in the related technology is solved. And in addition, the acetabular cup 20 is rotatably connected with the support seat 11 together, so owing to the above structure, a doctor may adjust a position of the acetabular cup 20 according to a practical condition of a patient, the acetabular cup 20 is guaranteed to be in a good installation angle and the problems of lower limb shortening and obvious deformity are improved.

In the embodiments, a side, contacted and matched with the ilium 1, of the connecting wing plate 12 is provided with a micropore structure (not shown in Fig.). It is proved by an animal experiment that the micropore structure has excellent bone integration capability. Therefore, the above-structure can implement the bone integration and reduces an incidence rate of nonunion.

Figure 1:
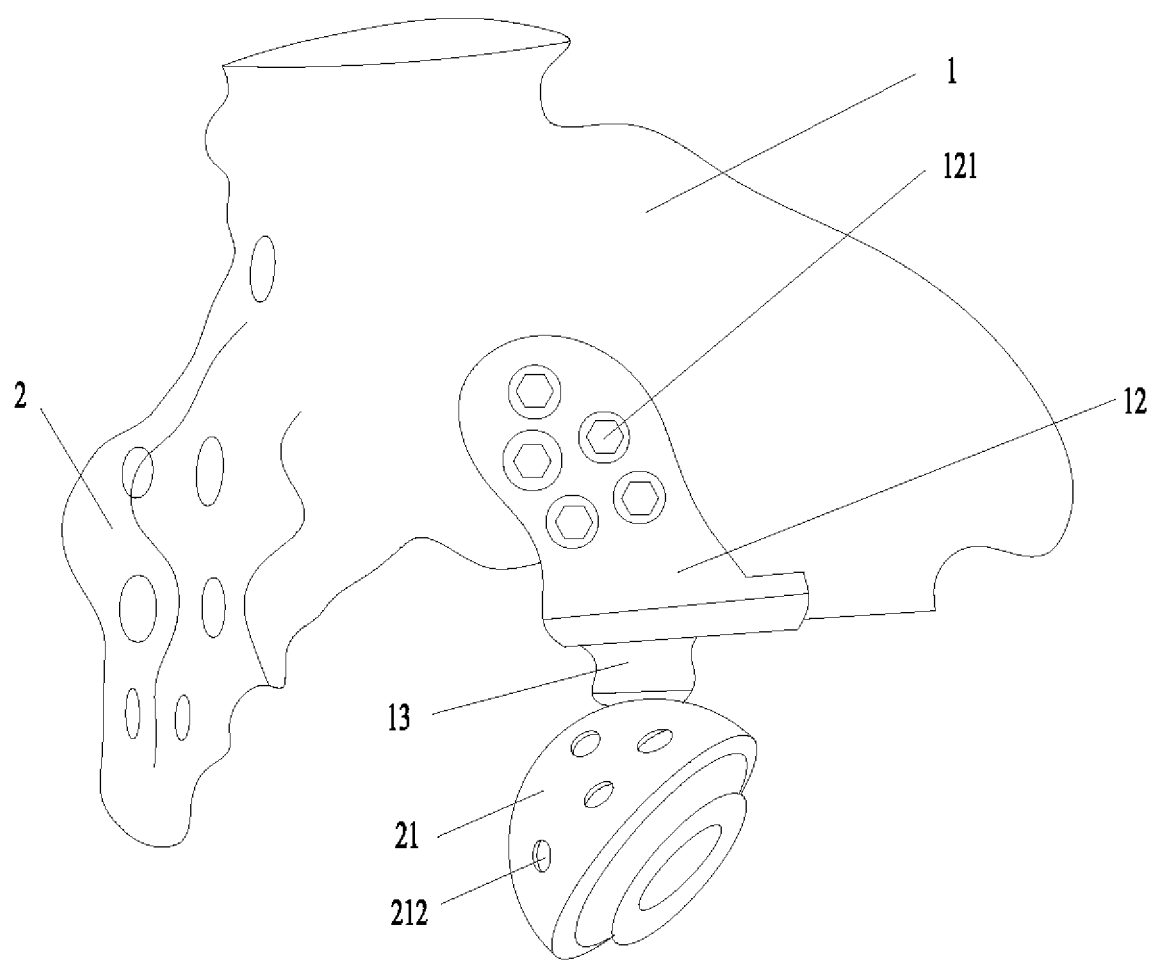
FIG. 1 depicts a three-dimensional structure schematic diagram of an embodiment of an acetabular defect reconstructive prosthesis of the present disclosure matched with an ilium.
Figure 2:
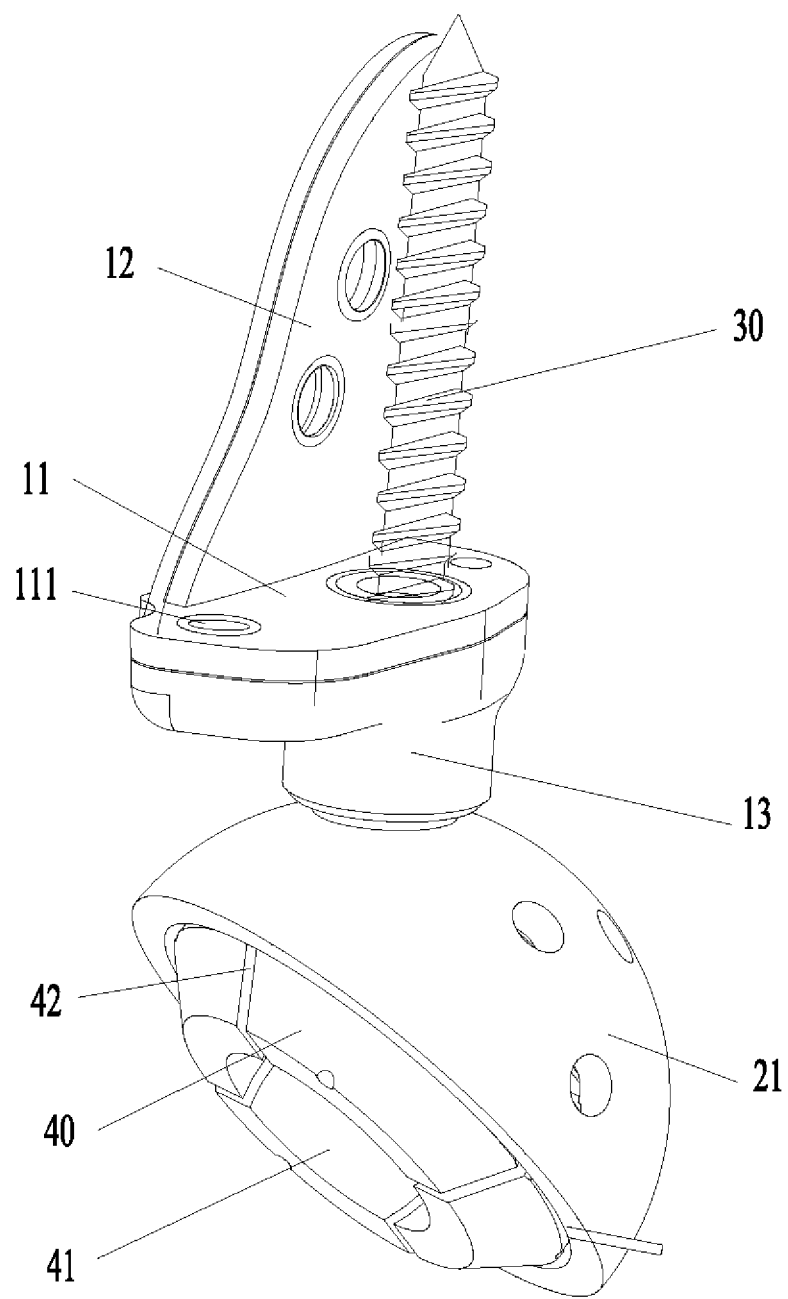
FIG. 2 depicts a three-dimensional structure schematic diagram of an angle of the acetabular defect reconstructive prosthesis in FIG. 1.
Figure 3:
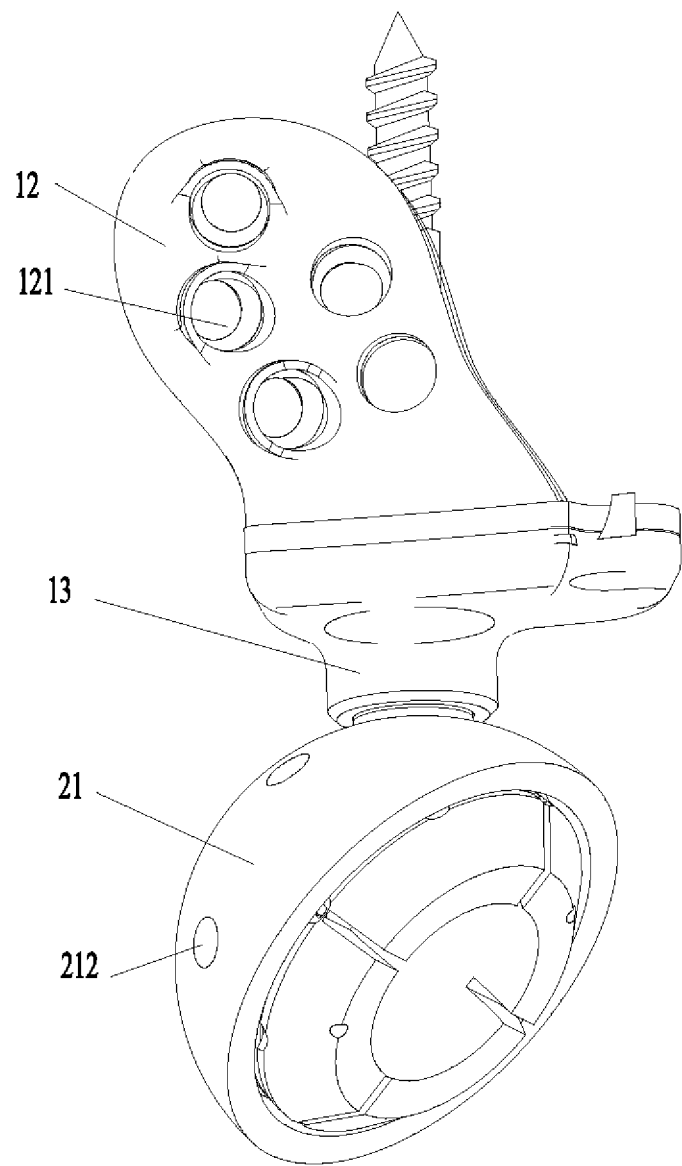
FIG. 3 depicts a three-dimensional structure schematic diagram of another angle of the acetabular defect reconstructive prosthesis in FIG. 1.

As shown in FIG. 1 to FIG. 3, in the embodiments, a plurality of first screw holes 121 are formed in the connecting wing plate 12; a plurality of first screw seats are respectively arranged in the first screw holes 121; and each of the first screw seats is provided with a spherical inner surface. When the doctor needs to fix the iliac support onto the ilium 1 via screws, the screws are penetrated into the first screw holes 121 first, and then the screws which go through the first screw holes 121 are placed into the high-level sacrum 2 via a sacroiliac joint. As each of the first screw hole 121 is conical holes, head portion of each of the screws is spherical head and each of the first screw seats is provided with the spherical inner surface matched with the spherical head, the screws can be rotated in a certain range, and the doctor may choose nailing directions of the screws in terms of a practical condition. With the above structure, the doctor can choose screw fixing positions according to the practical condition, so that the fixing effect between the iliac support and the ilium 1 is better.

It is to be noted that positions of the first screw holes 121 may be extracted by means of CT data of the patient.

In the embodiments, the side, contacted and matched with the ilium 1, of the connecting wing plate 12 and/or a side, contacted and matched with the ilium 1, of the support seat 11 are/is provided with a bio-coating (not shown in Fig.). The above structure can rapidly promote the generation of bone cells and is easily integrated with the bone (ilium), thereby achieving the medium-long term fixing effect. Compared with the traditional operation mode, it has the characteristics of high strength, high stability and strong bone integration capability, and reduces the incidence rate of the nonunion.

Figure 4:
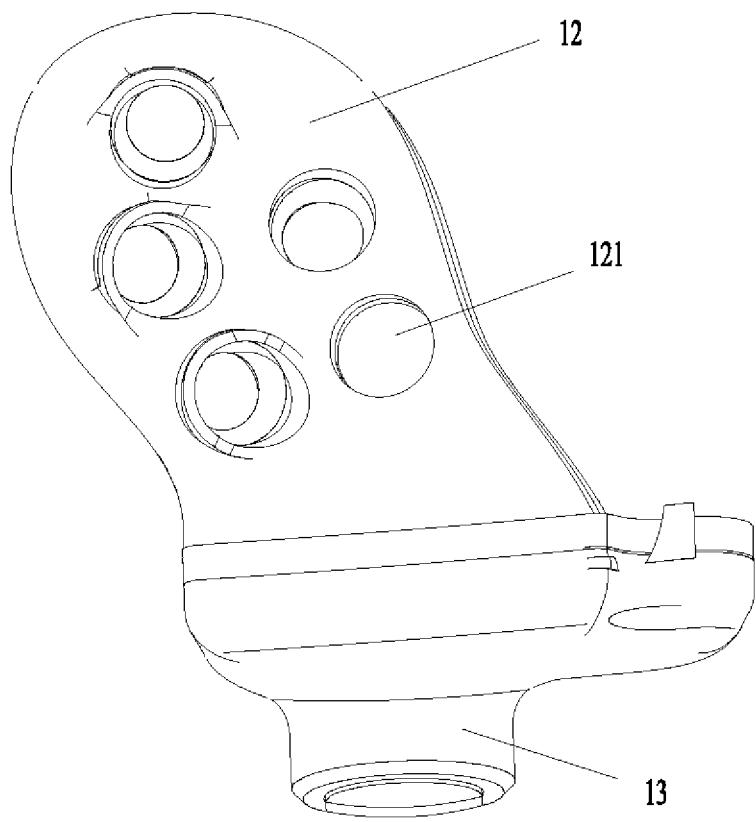
FIG. 4 depicts a three-dimensional structure schematic diagram of an iliac support of the acetabular defect reconstructive prosthesis in FIG. 1.
Figure 5:
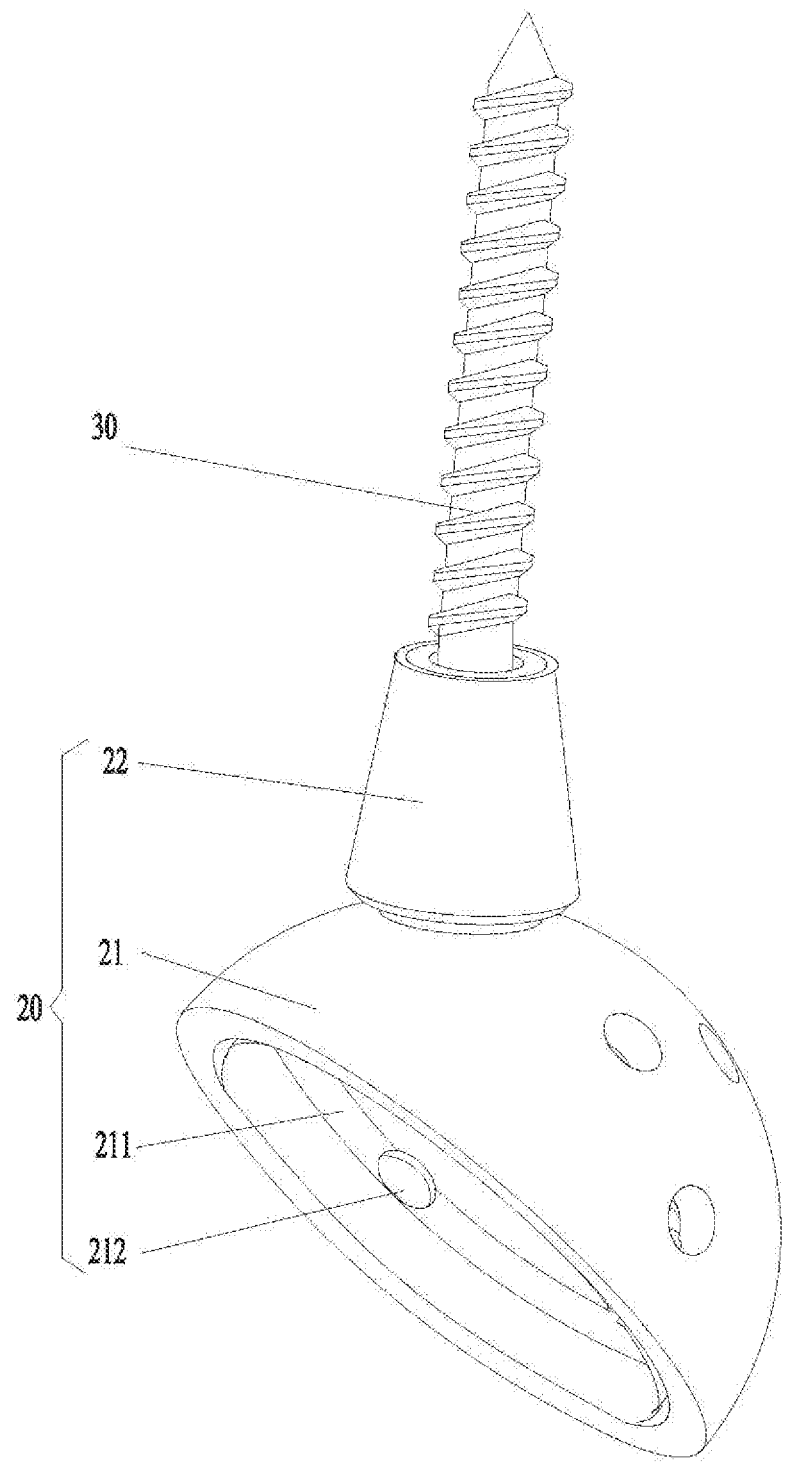
FIG. 5 depicts a three-dimensional structure schematic diagram of an acetabular cup of the acetabular defect reconstructive prosthesis in FIG. 1.
Figure 6:
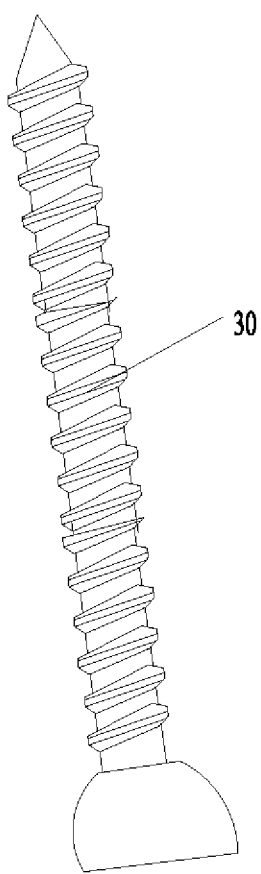
FIG. 6 depicts a three-dimensional structure schematic diagram of a fastening screw of the acetabular defect reconstructive prosthesis in FIG. 1.

As shown in FIG. 2, FIG. 4 and FIG. 5, in the embodiments, a first connection portion is provided on the support seat 11; and the acetabular cup 20 includes a cup body 21, and a second connection portion provided on the cup body and matched with the first connection portion. With the above structure, the support seat 11 is connected with the acetabular cup 20.

As shown in FIG. 2, FIG. 4 and FIG. 5, in the embodiments, the first connection portion is a first connecting cylinder 13; the second connection portion is a second connecting cylinder 22; and the first connecting cylinder 13 and the second connecting cylinder 22 are mutually nested together. Persons in the art should understood that when a diameter of an inner ring of the first connecting cylinder 13 is greater than that of an outer ring of the second connecting cylinder 22, the first connecting cylinder 13 is arranged out of the second connecting cylinder 22 in a sleeving manner; and when the diameter of the outer ring of the first connecting cylinder 13 is smaller than that of the inner ring of the second connecting cylinder 22, the second connecting cylinder 22 is arranged out of the first connecting cylinder 13 in a sleeving manner. The above structure is simple, and easy to machine. And in additional, it is ensured that an angle of the acetabular cup 20 can be adjustable in 360°.

As shown in FIG. 2, FIG. 4 and FIG. 5, in the embodiments, a conical hole is provided inside the first connecting cylinder 13; the connecting cylinder 22 is a conical cylinder; and the second connecting cylinder 22 is inserted into the first connecting cylinder 13. The first connecting cylinder 13 and the second connecting cylinder 22 are in a cone fit. With the above structure, the centering is good, i.e., axial lines of the first connecting cylinder 13 and the second connecting cylinder 22 have relatively high-precision coaxiality and both can be assembled and disassembled quickly.

As shown in FIG. 2, FIG. 3, FIG. 5 and FIG. 6, in the embodiments, the acetabular defect reconstructive prosthesis further includes a fastening screw 30; and the fastening screw 30 sequentially passes through the acetabular cup 20, the support seat 11 and the ilium 1 so that the acetabular defect reconstructive prosthesis is fixed on the ilium 1. The structure reinforces the fixing effect. And preferably, the fastening screw 30 in the embodiments is a lag screw.

As shown in FIG. 2, in the embodiments, a plurality of second screw holes 111 are formed in the support seat 11; a plurality of second screw seats are arranged in the second screw holes 111; and each of the second screw seats is provided with a spherical inner surface. When the doctor needs to fix the iliac support onto the ilium 1 via a screw, screws are penetrated into the second screw holes 111 first. Because each of the second screw holes 111 is a conical hole, a head portion of each of the screws is a spherical head and each of the second screw seats is provided with a spherical inner surface matched with the spherical head, the screws can be rotated in a certain range, and the doctor may choose a nailing direction of the screws in terms of a practical condition. With the above structure, the doctor can choose a screw fixing position according to the practical condition, so that the fixing effect between the iliac support and the ilium 1 is better.

It is to be noted that positions of the second screw holes 111 may be extracted by means of CT data of the patient.

In the embodiments, as shown in FIG. 3, an inner wall of the cup body 21 is spliced with hemi-spherical polyethylene linings 40 by means of bone cement. For ease of embedding the bone cement, as shown in FIG. 5, in the embodiments, an annular groove 211 is provided on the inner wall of the acetabular cup 20. And the above structure is simple and easy to implement.

As shown in FIG. 3, to better connect the acetabular cup 20 with the hemi-spherical polyethylene linings 40, in the embodiments, through holes 212 are provided on a cup wall of the cup body 21. With the above structure, the bone cement enters the through holes 212 to form a plurality of anchorings. And preferably, the number of the through holes 212 is 5-10.

Figure 7:
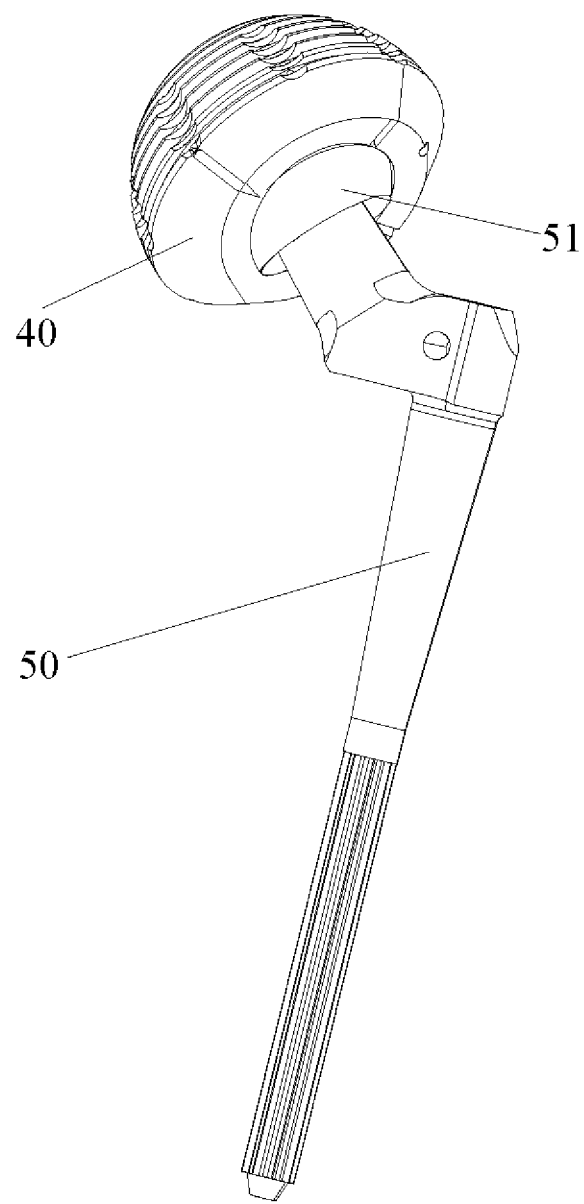
FIG. 7 depicts a three-dimensional structure schematic diagram for linings and a femoral stem matched with a cup body of the acetabular defect reconstructive prosthesis in FIG. 1.
Figure 8:
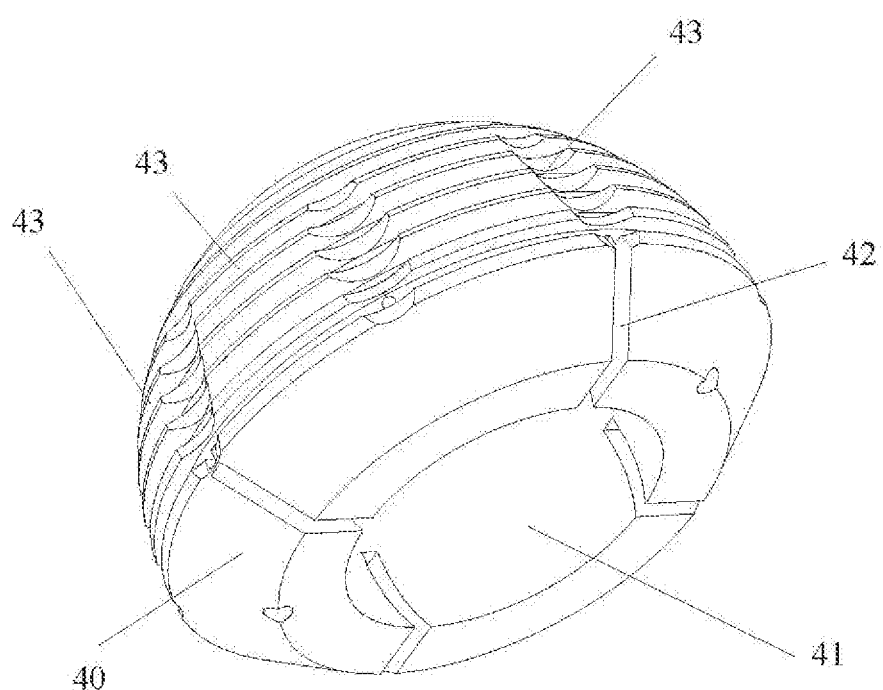
FIG. 8 depicts a three-dimensional structure schematic diagram of the linings in FIG. 7.

It is to be noted that, as shown in FIG. 7 and FIG. 8, the femoral stem 50 includes a spherical head 51; an installation space 41 for holding the spherical head 51 and lining grooves 42 are provided on the linings 40. When the spherical head 51 is hammered into the installation space 41, the lining grooves 42 are stretched out so as to ensure that the spherical head 51 can be smoothly hammered into the installation space 41. After the spherical head 51 is hammered into the installation space 41, the lining grooves 42 recover to an original state so as to prevent the spherical head 51 from dropping. Additionally, the linings 40 are of an over-radius design, so after the spherical head 51 is hammered into the installation space 41, most of the spherical head 51 is covered in the installation space 41, and thus, the spherical head 51 is not easily dropped out from the installation space 41.

Preferably, in the embodiments, the iliac support is of a hollow truss structure. On one hand, the truss structure can greatly reduce the weight of the iliac support and improves the material utilization rate, and simultaneously further can guarantee the strength and the rigidity of the iliac support. On the other hand, with the adoption of the above structure, the iliac support is closer to an adjacent skeleton, so that the bony fusion effect is better. Because anatomic reconstruction after the pelvic tumor excision needs to satisfy the accurate and complex requirements, and even further needs to satisfy the disposable and tailor-made requirements, the iliac support is prototyped by means of 3D printing in the embodiments. And the above process intrinsically has the characteristics of being accurate, being capable of manufacturing a complex part and being capable of personally customized.

It is to be noted that the connecting wing plate 12 is of a curved surface shape as a matter of fact. In the embodiments, for the purpose of attaching the connecting wing plate 12 to the ilium of the patient better, we may perform 3D reconstruction by means of the CT data of the patient to extract an iliac surface shape of the patient and then manufacture the connecting wing plate 12 with good attachment effect with the ilium by means of the iliac surface shape of the patient. By virtue of the above structure, the personal customization is implemented really. And as the iliac support is consistent with a skeleton of the patient, the good bone attachment and fixation may be implemented.

It is to be noted that a Three-Dimensional (3D) printing rapid prototyping technology is a brand-new manufacturing technology based on a material stacking method, is different from the traditional removed material processing technology, and is also referred to as additive manufacturing (AKYCM, AKYCdditive MAKYCnufAKYCcturing). The 3D printing technology is to stack layers of a material into an entity via a rapid prototyping machine by employing 3D CAKYCD data. It is named because though different types of rapid prototyping systems have different prototyping principles and system characteristics depending on different prototyping materials used, their basic principles are the same and are to "manufacture in layers and overlap one by one", just like a "3D printer". With the rapid development of cutting-edge technologies such as manufacturing technology, digital modeling technology, numerical control technology, information technology, material science technology, chemical and biological technologies as well as the multidisciplinary close cooperation, the development of the 3D printing technology has become one of the most popular new technologies at present. The 3D printing will have a broad application prospect in the orthopedics field in future because its characteristics meet special requirements of the orthopedics. On one hand, bone tissues are a typical example of a complex structure, and it is very hard for the existing bionic technology to copy their special 3D forms and physiological functions. However, the 3D printing is just suitable for the rapid manufacturing of the complex structure and can obtain an approximately ideal bone repair material. And on the other hand, human bodies have a highly individual specificity, the traditional medical products produced in large scale and in batches cannot meet the personalized requirement and the former personalized and customized products produced by means of a manufacturing process such as mould have a high cost and a long period. Following the widespread application of a digital imaging technology in the medical field, the skeleton is an organ easiest to obtain an accurate digital image; and by combining with the skeleton and the 3D printing, the personalized medical products may be produced accurately and rapidly at a low cost. Therefore, by virtue of the 3D printing technology, an implant product with any form and an ideal biomechanical strength can be casted in a short time, making the development of personalized and customized bone implant products become true.

The above description is only preferred embodiments of the present disclosure and is not intended to limit the present disclosure. Persons in the art can make various modifications and changes of the present disclosure. Any modification, equivalent replacement, or improvement made within the spirit and principle of the present disclosure shall all fall within the protection scope of the present disclosure.

What is claimed is:

1. An acetabular defect reconstructive prosthesis, comprising:
    an iliac support, the iliac support comprising a support seat (11) and a connecting wing plate (12) provided on the support seat (11), and the support seat (11) being contacted and matched with an ilium (1); and
    an acetabular cup (20) rotatably connected with the support seat (11) together, a first connection portion is provided on the support seat (11); and the acetabular cup (20) comprises a cup body (21), and a second connection portion provided on the cup body (21) and matched with the first connection portion, the first connection portion is a first connecting cylinder (13); the second connection portion is a second connecting cylinder (22); and the first connecting cylinder (13) and the second connecting cylinder (22) are mutually nested together, an inner wall of the cup body (21) is spliced with hemi-spherical polyethylene lining (40) by means of bone cement, through holes (212) are provided on a cup wall of the cup body (21), so that the bone cement enters the through holes (212) to form a plurality of anchoring structures, a surface of the hemi-spherical polyethylene lining (40) facing the cup body (21) is provided with multiple receiving grooves (43) to receive the bone cement, an installation space (41) for holding a spherical head (51) and lining grooves (42) are provided on the hemi-spherical polyethylene lining (40).

2. The acetabular defect reconstructive prosthesis as claimed in claim 1, wherein a side, contacted and matched with the ilium (1), of the connecting wing plate (12) is provided with a micropore structure.

3. The acetabular defect reconstructive prosthesis as claimed in claim 1, wherein a first screw hole (121) is formed in the connecting wing plate (12); a first screw seat is arranged in the first screw hole (121); and the first screw seat is provided with a spherical inner surface.

4. The acetabular defect reconstructive prosthesis as claimed in claim 1, wherein the side, contacted and matched with the ilium (1), of the connecting wing plate (12) and/or a side, contacted and matched with the ilium (1), of the support seat (11) are/is provided with a bio-coating.

5. The acetabular defect reconstructive prosthesis as claimed in claim 1, wherein a conical hole is provided inside the first connecting cylinder (13); the second connecting cylinder (22) is a conical cylinder; and the second connecting cylinder (22) is inserted into the first connecting cylinder (13).

6. The acetabular defect reconstructive prosthesis as claimed in claim 1, wherein the acetabular defect reconstructive prosthesis further comprises a fastening screw (30); and the fastening screw (30) sequentially passes through the acetabular cup (20), the support seat (11) and the ilium (1) so that the acetabular defect reconstructive prosthesis is fixed on the ilium (1).

7. The acetabular defect reconstructive prosthesis as claimed in claim 1, wherein a second screw hole (111) is formed in the support seat (11); a second screw seat is arranged in the second screw hole (111); and the second screw seat is provided with a spherical inner surface.

8. The acetabular defect reconstructive prosthesis as claimed in claim 1, wherein the connecting wing plate (12) is of a curved surface shape.

* * * * *